United States Patent
Nishimura et al.

(10) Patent No.: US 6,476,162 B1
(45) Date of Patent: Nov. 5, 2002

(54) METHOD FOR PREVENTING EASILY POLYMERIZING SUBSTANCE FROM POLYMERIZATION AND METHOD FOR PRODUCTION OF (METH) ACRYLIC ACID OR ESTER THEREOF

(75) Inventors: Takeshi Nishimura, Himeji (JP); Kazuhiko Sakamoto, Himeji (JP); Kenji Sanada, Himeji (JP); Masakatsu Mori, Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/880,396

(22) Filed: Jun. 13, 2001

(51) Int. Cl.$^7$ .................................................. C08F 2/38
(52) U.S. Cl. ...................... 526/82; 526/77; 526/317.1; 526/319
(58) Field of Search .................. 526/77, 82, 317.1, 526/319

(56) References Cited

U.S. PATENT DOCUMENTS 4,724,126 A * 2/1988 Dinbergs et al. ............ 422/131
5,635,035 A    6/1997 Koshy

FOREIGN PATENT DOCUMENTS

| | | |
|---|---|---|
| EP | 0 307 074 A2 | 7/1987 |
| EP | 0 803 277 | 10/1997 |
| EP | 0 982 290 A2 | 3/2000 |
| EP | 1 034 824 A2 | 9/2000 |
| EP | 1 035 102 A1 | 9/2000 |
| EP | 1 093 850 A2 | 4/2001 |
| EP | 1093850 A2 * | 4/2001 |
| JP | A-53-125969 | 11/1978 |

OTHER PUBLICATIONS

"Chemical Engineering" (Sep., 1980) pp. 32–36, pp. 53–55 and partial translation thereof.

JP–A–1–180850 and partial translation thereof.

* cited by examiner

Primary Examiner—David W. Wu
Assistant Examiner—William Cheung
(74) Attorney, Agent, or Firm—Mathews, Collins, Shepherd & McKay, P.A.

(57) ABSTRACT

In a packed column handling an easily polymerizing substance, the packing with which the column is stuffed is subjected to a water-repelling treatment or a wetting treatment to prevent the easily polymerizing substance in the packed column from polymerizing. By preventing the occurrence of a polymer, it is made possible to ensure continuous production of an easily polymerizing substance-containing solution and decrease the content of the easily polymerizing substance in the product and consequently improve the quality of the product.

7 Claims, No Drawings

METHOD FOR PREVENTING EASILY POLYMERIZING SUBSTANCE FROM POLYMERIZATION AND METHOD FOR PRODUCTION OF (METH) ACRYLIC ACID OR ESTER THEREOF

BACKGROUND OF THE INVENTION

1. Field of the Invention

This invention relates to a method for preventing easily polymerizing substance from polymerization in a packed column, and more particularly to a method for preventing from polymerization in a packed column using a packing having undergone a water-repelling treatment or a wetting treatment from inducing polymerization and a method for the production of (meth)acrylic acid or an ester thereof in the packed column having the packing disposed therein.

2. Description of the Related Art

Such easily polymerizing compounds as acrylic acid and methacrylic acid are raw material for commercial production and are chemical substances to be produced in large volumes at plants in large scale. In the case of (meth)acrylic acid, for example, such easily polymerizing compounds are produced by the reaction of catalytic gas phase oxidation of propylene, isobutylene, t-butanol, methyl-t-butyl ether, and acrolein.

In the reaction gas which is obtained by the reaction of catalytic gas phase oxidation, however, by-products of (meth)acrylic acid, a target product, are present in a mixed state. This reaction, for example, generates mainly non-condensable gases, namely unaltered propylene and isobutylene, low-boiling organic compounds having lower boiling points than acrylic acid, namely steam, unaltered acrolein, formaldehyde produced by a side reaction, and impurities such as acetic acid, and high-boiling compounds having higher boiling points than acrylic acid, namely maleic anhydride, furfural, benzaldehyde, benzoic acid, and acrylic acid dimer. For the purpose of purifying the target product, therefore, rectification and fractional distillation are carried out with various distilling columns.

Generally, in the distilling column, the vapor abounding in the low-boiling component and ascending to the top of the distilling column is cooled and condensed, the condensate is fallen from the top of the column and allowed to contact the vapor ascending from below and induced gasification of the low-boiling component included in the condensate, and at the same time the high-boiling component in the vapor is condensed and liquefied. As a result, the distilling column increases the purity of the low-boiling component of the vapor departing from the top of the column and, at the same time, increases the purity of the high-boiling component of the liquid falling to the bottom of the column.

The packed column which is one type of the distilling column types a device in popular use because it is at an advantage in having a simple structure, allowing easy manufacture, and incurring only small pressure loss of gas. In the packed column, various kinds of packing are used as a high-performance device for mass transfer for the purpose of saving energy improving the yield of products, increasing the amount of treatment, and decreasing pressure loss and for the elimination of such troubles as foaming and entrainment of mist. Particularly in the purification of an easily polymerizing substance, the packing is used for the purpose of exalting the property of separation.

The packing is regularly or irregularly disposed inside the column, for example, and used for causing the liquid descending from the upper part of the column and the vapor ascending from the lower part thereof to establish gas-liquid contact in a cruciform or counterflow pattern on the surface of the packing. Consequently, the gas-liquid contact surface is enlarged enough to allow thorough material transfer between the vapor and the liquid and accomplish efficient material separation.

The packing heretofore used in the packed column, however, has been only required to satisfy such conditions as manifesting a wide specific surface area, a large percentage of voids, high mechanical strength, a small apparent density, and high resistance to corrosion and enjoying inexpensiveness. The operation of material transferring by gas-liquid contact in the packed column which handles a solution containing an easily polymerizing substance, therefore, has possibly given generation of a polymer owing to the inferior contact between the gas and the liquid.

When acrylic acid is produced by the catalytic gas phase oxidation of propylene and/or acrolein with a molecular oxygen-containing gas, for example, the acrylic acid-containing liquid is unusually liable to induce the acrylic acid to polymerize because it contains such impurities as water, acetic acid, and acrolein. Generally for the purpose of preventing this polymerization, various polymerization inhibitors such as hydroquinone, p-methoxy phenol, and phenothiazine are added to the process of production either singly or in the form of a combination of two or more members and enabled to repress the polymerization of acrylic acid, etc. Since these inhibitors have higher boiling points than the easily polymerizing substance and are not contained in the vapor of distillation, they fail to prevent efficiently the polymerization of the easily polymerizing substance. The column, therefore, incurs the mishap of polymerization in the interior thereof, degrades the efficiency of the purification by separation, deteriorates the quality of the product and, at the same time, obstructs the continued operation of the column owing to the adhesion of the polymer to the devices and the blockage of the gas-liquid paths.

This situation necessitates early removal of the polymer. The removal of the polymer compels the process of purification to be suspended. The removal of the polymer adhering to the inner surface of the column is generally difficult.

Further, the packed column is of ten attached a reboiler to the bottom of the column. Through this reboiler, not only the vapor but also the bottom liquid of the column being circulated via the reboiler is blown in copiously. There is a case where the vapor of the target of purification ascends the interior of the distilling column in accordance with the ascending speed in the column and, at the same time, entrains the splash of the bottom liquid of the column and carries it as far as the bed of the packing in the column. Since part of the bottom liquid of the column mingles the product of distillation through the top of the column, the efficiency of the separation by distillation is possibly deteriorated. Particularly, when the polymer adheres to the packing in the packed column, the treatment for the removal of the adhering polymer necessitates great labor.

In the packed column which is used particularly for the expulsion of the easily polymerizing substance by distillation and the purification of the product by separation, therefore, a method for obtaining the target product with a high degree of purification while maintaining the purification of the product by separation of the easily polymerizing substance and preventing the easily polymerizing substance from yielding to polymerization has been desired.

SUMMARY OF THE INVENTION

The present inventor, as a result of pursuing an elaborate study regarding the packing intended to fill the packed column, has found that, by subjecting the surface of the packing to a water repelling treatment or a wetting treatment, the mishap of polymerization of the easily polymerizing substance can be prevented without degrading the efficiency of separation owing to the gas-liquid contact. This invention has been perfected as a result.

Specifically, this invention is aimed at providing the following items (1) or (2).

(1) A method for preventing an easily polymerizing substance from exposing the substance to polymerization in a packed column handling the easily polymerizing substance, characterized by subjecting the surface of a packing disposed in the interior of the column to a water repelling treatment or a wetting treatment.

(2) A method for the production of (meth)acrylic acid or an ester thereof, characterized by purifying at least one member selected from the group consisting of acrylic acid, methacrylic acid, and esters thereof in the presence of a polymerization inhibitor in a packed column having disposed therein a packing having at least part of the surface thereof subjected to a wetting treatment or a water-repelling treatment.

According to this invention, by subjecting the surface of a packing disposed in a packed column to a water-repelling treatment or a wetting treatment, it is made possible to repress the occurrence of a polymer on the surface of the packing. By the treatment, it is made possible also to prevent adhesion of a polymerizing substance. In the purification of an easily polymerizing substance, the substance owing to the chemical property thereof forms a polymer in a distilling column and this polymerization imposes a limit on the continuous operation of the column and compels the removal of the polymer from the column during the suspension of the operation thereof to consume huge time and cost. According to this invention, the problem mentioned above can be easily solved by giving the packing a water-repelling treatment resorting to a shot blast or a treatment for lowering Ry up to not more than 12.5 as published in JIS (Japanese Industrial Standards) B601 (-1994).

Further, by the method of production according to this invention, it is made possible to produce acrylic acid, methacrylic acid, or an ester thereof to be stably produced by a continuous operation without exposing the product to inclusion of such impurities as polymer.

DETAILED DESCRIPTION OF THE
PREFERRED EMBODIMENTS

The first aspect of this invention concerns a method for preventing an easily polymerizing substance from exposing the substance to polymerization in a packed column handling the easily polymerizing substance, characterized by subjecting the surface of a packing disposed in the interior of the column to a water repelling treatment or a wetting treatment.

The packing disposed in the packed column is used for the purpose of enlarging the gas-liquid contact surface in the column and consequently exalting the efficiency of the gas-liquid contact. Thus, for the purpose of improving the efficiency with which the refluxing liquid is separated from the surface of the packing, it is necessary for the refluxing liquid to be spread on the surface of the packing and retained on the surface of the packing for a prescribed time enough for thorough gas-liquid contact. The refluxing liquid retained on the surface of the packing is the product which has occurred during the condensation of this liquid together with the easily polymerizing substance distilled in advance of the condensation. Even when the bottom liquid of the column uses the polymerization inhibitor therein, the refluxing liquid does not contain therein the polymerization inhibitor which is a high-boiling substance and consequently the easily polymerizing substance on the surface of the packing tends to give rise to a polymer.

The present inventor has found, however, that when a water-repelling treatment or a wetting treatment is performed thoroughly on the surface of the packing, the degradation of the efficiency of separation can be avoided and the polymerization of the easily polymerizing substance can be prevented from occurring as well. Further, by this treatment, the adhesion itself of the polymer to the packing can be repressed. It has never been predicted heretofore that the small improvement in the surface of the packing should bring such a prominent effect as this. Thus, it is made possible to repress effectively the occurrence of the polymer in the packed column and the blockage of the column with the polymer and enable the column to be operated continuously for a long time. Now, this invention will be described in detail below.

The packing to be used in this invention does not need to be particularly discriminated but is only required to have undergone a water-repelling treatment or a wetting treatment. The term "wetting treatment" as used in this invention means a treatment such that the surface of the packing which has undergone the treatment, even when wetted with the solvent used in the column and further with the solution containing the target product of purification, shows no visually discernible sign of repellency of liquid. The water-repelling treatment embraces a treatment which resides in lowering the roughness of part or the whole of the surface of a packing which has undergone the treatment to a level of not more than Ry 12.5 as determined by the method specified in JIS B601 (-1994). The wetting treatment and the water-repelling treatment under discussion are not equal in real nature. It has been discovered in this invention that by either of these treatments, it is made possible to repress the occurrence and the adhesion of the polymer on the surface of the packing. Thus, these treatments are both favorable. The wetting treatment can effectively repress the occurrence of the polymer on the surface of the packing because the packing retains fully satisfactorily on the surface thereof the easily polymerizing substance-containing solution in the refining column which has contained the polymerization inhibitor. In contrast, the water-repelling treatment is considered favorable because it is capable of preventing the polymerization by immediately repelling the easily polymerizing substance-containing solution from the surface of the packing and expelling it from the surface of the packing. Particularly, the wetting treatment can decrease the minimum liquid flow volume and accomplish the purification by efficient material separation.

The wetting treatment in this invention is implemented by subjecting the surface of the packing to shot blast, sand blast, tumbler, for example.

Inherently, the shot blast, sand blast, and tumbler are treatments for removing sand adhering to a cast article. In this invention, it has been found that when such treatments are adopted for inflicting scars on the surface of the packing, the packing is enabled to retain the easily polymerizing substance-containing solution satisfactorily. Though the reason for the wetting treatment to permit such efficient prevention of the polymerization remains yet to be elucidated, this prevention may be logically explained by a supposition that the polymerization is prevented because the easily polymerizing substance-containing solution which has admitted the polymerization inhibitor added during the purification of the easily polymerizing substance in the packed column is retained on the surface of the packing. It is further supposed that the efficiency of the purification is also improved because the solution subjected to the purification is retained fully satisfactorily on the surface of the packing and consequently the gas-liquid separation is effected efficiently.

The shot blast treatment contemplated herein consists in throwing shots made of iron and grids formed by cutting a wire at a given cast article by means of a vane wheel of a device. The shot blast device, therefore, is generally used in cleaning the skin of a cast article after the removal of sand. It is occasionally used for causing a cast article to shed the sand adhering thereto. The device of this nature is referred to as "a powerful shot blast device" or "a core knockout device." This invention can use the device known heretofore as intended for use in the shot blast treatment. In this invention, the shot blast treatment known heretofore as intended for the wetting treatment is not specified by the rotational frequency of the vanes of the device, the speed of throwing of shots, the size of shots, and the duration of the treatment. The effect of the surface treatment manifests itself in the state in which the whole of the surface, when sprinkled with water, is amply wetted without repelling any liquid.

The sand blast is intended to clean the surface of a given article by spouting sand against the surface through a nozzle with air projected under a pressure in the range of 0.2–0.5 MPa. The tumbler is intended to clean a given article by placing this article and polygonal iron grains in a rotary drum and tumbling them together by the rotation of the rotary drum. Though the duration of one round of such a treatment does not need to be particularly limited, it is in the approximate range of 0.5–1 hour where the rotational frequency is in the range of 0.7–1/s. The drum is furnished with holes 10–15 mm in diameter in such a manner that the sand falls down through the holes. The iron grains in popular use have a size in the range of 15–20mm, though not exclusively.

This invention is preferred to use the shot blast particularly as the method for the surface treatment of the packing. The reason for this preference is that the shot blast, by cleaning the surface of the packing or inflicting scars to a certain degree on the surface, improves simply the packing in the condition of wetting with a liquid and enables the surface of the packing to retain the liquid fully satisfactorily. Further, the irregularities of the surface adds to the amount of the holdup of the liquid and enhances the efficiency of separation. Specifically, the amount of the holdup of the liquid in the packed column is expressed by the volume of the liquid per unit volume of the packing bed and the holdup corresponding to the total amount of the liquid in the column is considered to be the sum of the dynamic holdlup corresponding to the amount of the liquid flowing down and the static holdup corresponding to the amount of the liquid existing stationarily in the column. According to the shot blast treatment mentioned above, since the surface is wetted, the retention time of the easily polymerizing substance-containing solution on the surface is elongated and consequently the total amount of the holdup of the liquid is kept intact and, as a result, the efficiency of the liquid-gas separation is retained at a high level.

To explain the relation between the packed column and the feed tray for the raw material, the feed tray for the raw material is not discriminated on account of their position but may exist anywhere in the packed column. Generally, the packed column is attached a condenser approximately the top of the column and attached a reboiler approximately the bottom of the column. Reflux liquid is introduced into the column form the condenser and bottom liquid of the column is boiled up and generated vapor by the reboiler. Regardless the position of the feed for the raw material, the column is filled with such gas-liquid mixed system thereby separating and refining the object compound. That is, the packings are always disposed in such liquid-gas system in the packed column with the consequence that the surface of the packing repeats between in a state wetted with the liquid and exposed in the gas. In this invention, when the packing has undergone the wetting treatment, the surface of the packing is preferred to be thoroughly wetted with the liquid. The effect of this invention in preventing the polymerization excels particularly when the solution contains the polymerization inhibitor on the other hand, when a polymerization inhibitor which is liable to volatilize in the gas phase is additionally used, since the polymerization inhibitor is volatilized into the gas phase, the polymerization on the surface of the packing existing in the gas phase can be prevented more effectively.

In this invention, the water-repelling treatment can prevent the polymerization itself of the easily polymerizing substance because this treatment curtails the retention time of the easily polymerizing substance-containing solution adhering to the surface of the packing. When this treatment adjusts the surface roughness, Ry, of not more than 12.5 as determined by the method specified in JIS B601 (-1994), the retention of the solution on the surface of the packing can be eliminated because the solution adhering to the surface of the packing is quickly repelled in the packed column. Particularly when the solution just mentioned happens to be the condensate in the gas phase which does not contain the polymerization inhibitor, this situation is very liable to generate the polymer. This invention can prevent this polymerization by the water-repelling treatment. The water-repelling treatment, therefore, is effective for the packing disposed on either of the gas phase side and the liquid phase.

For the purpose of enabling this water-repelling treatment to adjust the magnitude Ry of not more than 12.5 as specified by JIS B601 (-1994), the treatment must resort to the mechanical abrasion such as buffing or the electrolytic abrasion.

The buffing is a method of abrasion which is mainly used in obtaining a smooth surface or a glossy surface. The crude abrasion using a solid abrasive material, the intermediate abrasion using a semi-solid or free abrasive material, and the finishing abrasion are available for the buffing. The buffing materials which are usable herein include such flexible materials as leather and cloth, tripolysilica stone, chromium oxide, silicon carbide, fused alumina, burnt alumina, and oily or nonoily spraying agent containing chromium oxide as an abrading material.

The electrolytic abrasion is a method for simultaneously melting and smoothing a metallic surface. As the electrolytic abrading solution to be used when the packing is made of iron or steel or stainless steel, perchloric acid type, sulfuric acid type, phosphoric acid type, and sulfuric acid-phosphoric acid type solutions are available. Since the iron or steel is not merely varied in composition but also widely varied in texture with the degree of heat treatment and working, it may be properly selected so as to suit the packing to be used. The amount of the acetic anhydride generally added to the perchloric acid type electrolyte, the temperature of electrolysis, the current density, the voltage, and the duration of electrolysis may be properly selected to suit the packing to be actually used. Optionally, the mechanical abrasion may be performed and the treatment of electrolytic abrasion may be further carried out. Thus, by buffing a given packing and lowering the surface roughness by such a method as electrolytic abrasion, the polymerization can be prevented because the surface of the packing is thoroughly prevented from drying.

Such factors of the packing for use in this invention as shape, size, and raw material may be properly selected so as to suit the size and the shape of the packed column to be actually used and the purpose for which the packed column is used. The raw material does not need to be particularly discriminated. The packing is preferred, however, to be made of alumina, stainless steel, or some other metal. The reason for preference of such a material is that this material is incapable of reacting with an easily polymerizing substance, affecting the easily polymerizing substance, or inducing the packing itself to corrode.

The magnitude of Ry of the packing of this invention as specified in JIS B601(-1994) is preferably not more than 12.5 and more preferably not more than 3.2. If this magnitude exceeds 12.5, the excess will be at a disadvantage in readily inducing the easily polymerizing substance-containing solution to stagnate and consequently possibly giving rise to a polymer. Though the whole surface of the packing is preferred to have the magnitude of Ry thereof adjusted at a level of not more than 12.5 as specified in JIS B601 (-1994), there is a time when the treatment for fulfilling this requirement proves difficult on account of the shape of the packing. In this invention, therefore, at least part of the surface is required to meet the standard that the magnitude of Ry specified in JIS B601 (-1994) should be not more than The packing for use in this invention is preferred to be made of such a metallic material as alumina or stainless steel. The reason for this choice of the metallic material is that the decrease of pressure loss, for example, is demanded from the viewpoint of the durability under the influence of increased pressure and elevated temperature and the efficiency of production because the purification of the easily polymerizing substance-containing solution necessitates application of heat for the sake of distilling the substance and further the purification of the general purpose raw material necessitates purification of a large amount of feed stock all at once. The avoidance of reaction with the feed stock to the packed column also forms an important factor. In this respect, the stock which is made of such a metallic material as alumina or stainless steel excels in the formability and satisfies the requirement mentioned above.

The packing for use in this invention does not need to be particularly discriminated on account of the shape and the designation. The packing in any shape can be favorably used. The packings which are favorably used herein include well-known rasching rings, Lessing rings, pall rings, flexirings, cascade-mini-rings, rasching super rings, intalox metal tower packings, and intalox saddles, the packings which are published in Kagaku Kougaku Binran (compiled by the society of chemical engineers, Japan), ed. 6, page 604, FIGS. 11–13, mellapak, gempaks, techno pack, monzpak, interlocks high-performance structured packings, and flexipac, and regular packs of a metallic sheet type published in Kagaku Kougaku Binran (compiled by the society of chemical engineers, Japan), ed. 6, page 567, for example. The diameter, shape, material, etc. of the packing to be actually used may be properly selected, depending on the size of the packed column in actual use, the kind of feed stock and the amount of supply, the temperature conditions, the pressure conditions, the theoretical number of steps, the pressure loss, the lowest flow volume, and other factors. The rasching rings, Lessing rings, pall rings, flexiring, cascade-mini-rings, rasching super rings, interlocks metal tower packings, and interlock saddles are used advantageously as packings in this invention, because they invariably have a large surface area and a high percentage of voids they can perform mass exchange efficiently and can decrease the pressureloss. Among other kinds of packings enumerated above, the cascade-mini-rings can be used particularly favorably. The reason for the choice of this kind of packing is that this packing has a high surface area per $m^3$ and excels in the percentage of voids.

The packed column which is aimed at by this invention is stuffed regularly or irregularly with a given packing which is mounted on a packing support therein. The column itself does not need to discriminate the purpose of use thereof. The uses found for such columns possibly include distillation, extraction, absorption, stripping, and reaction. The columns, therefore, are occasionally designated as distilling column, absorbing column, and extracting column, for example.

The packed column of this kind does not need to be particularly restricted. The packed columns known to the art may form the targets of this invention. In this invention, however, the packing with which the packed column is stuffed is preferred to have a surface coarseness, Ry, specified in JIS B601 of not more than 12.5. The reason for this particular surface roughness is that when the interior of the packed column has such a specified surface roughness, the packing rapidly repels the liquid from the surface and eliminates the stagnation of the liquid.

As concrete examples of the packing which fills the packed column, liquid distributors, flash feed predistributors, collectors, vapor spargers, packing supports, and hold down grids may be cited. For the purpose of enabling such a packing material to fulfill the requirement that the magnitude of Ry should be not more than 12.5 as specified in JIS B601, it suffices to perform the mechanical abrasion such as buffing or the electrolytic abrasion on the packing material.

This invention is characterized by consisting in a packed column particularly adapted to handle an easily polymerizing substance. The easily polymerizing substance for use in this invention does not need to be discriminated between a gas or a liquid. As concrete examples of the easily polymerizing substance, acrylic acid, methacrylic acid, maleic anhydride, and esters thereof, and styrene and acrylonitrile may be cited. The acrylic esters usable herein include methyl acrylate, ethyl acrylate, butyl acrylate, 2-ethylhexyl acrylate, 2-hydroxyethyl acrylate, and 2-hydroxypropyl acrylate, for example. The methacrylic esters which are usable herein include methyl methacrylate, butyl methacrylate, 2-hydroxyethyl methacrylate, and 2-hydroxypropyl methacrylate, for example.

The easily polymerizing substance-containing solution may further contain solvents, high boiling substances, and mixtures of easily polymerizing substance with by-products which occur during the formation of the easily polymerizing substance. Particularly favorably, the easily polymerizing I substance is acrylic acid, methacrylic acid, or an ester thereof. The easily polymerizing substance-containing solution contemplated by this invention is allowed to contain further a solvent and other impurities. As concrete examples of such impurities, propionic acid, acrolein, maleic acid, water, and formalin may be cited, which are by-produced in obtaining by the reaction of catalytic gas phase oxidation either acrylic acid or an acrylic ester, i.e. as an easily polymerizing substance, may be cited. Where the easily polymerized substance happens to be methacrylic acid or a methacrylic ester, methacrolein, acrylic acid, and acetic acid which are by-produced in obtaining methacrylic acid by the reaction of catalytic gas phase oxidation may be cited as impurities.

The solvent is allowed to incorporate therein a compound which is generally known as a polymerization inhibitor for such an easily polymerizing substance as acrylic acid for the purpose of preventing the easily polymerizing substance, i.e. (meth)acrylic acid, from polymerizing.

As concrete examples of the polymerization inhibitor, such known compounds as nitroso compounds, N-oxyl compounds, N-hydroxy-2,2,6,6-tetramethylpiperidine compounds, 2,2,6,6-tetramethylpiperidine compounds, phenol compounds, phenothiazine compounds, copper salt compounds, and manganese salt compounds may be cited. These polymerization inhibitors may be used either singly or in the form of a combination of two or more members.

As concrete examples of the nitroso compound, N-nitrosophenylhydroxylamine and ammonium salts thereof, p-nitrosophenol, N-nitrosodiphenylamine may be cited.

The N-oxyl compounds do not need to be particularly discriminated. Generally, N-oxyl compounds which are known as polymerization inhibitors for vinyl compounds may be invariably used. Among other N-oxyl compounds, the group of 2,2,6,6-tetramethylpiperidinoxyls which are represented by the following formula (1) are used particularly favorably.

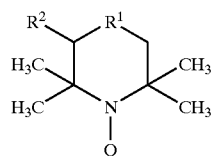

(1)

(wherein $R^1$ represents CHOH, $CHCH_2OH$, $CHCH_2CH_2OH$, $CHOCH_2OH$, $CHOCH_2CH_2OH$, CHCOOH, or C=O and $R^2$ represents H or $CH_2OH$). The N-oxyl compound to be used herein does not need to be particularly discriminated but is only required to be an N-oxyl compound at all. It is advantageous to use one member or a combination of two or more members selected from the group consisting of 2,2,6,6-tetramethylpiperidinoxyl, 4-hydroxy-2,2,6,6-tetramethylpiperidinoxyl, and 4,',4"-tris-(2,2,6,6-tetramethylpiperidinoxyl) phosphite which can afford a prominent effect in the prevention of the polymerization. Particularly when 2,2,6,6-tetramethylpiperidinoxyl or 4-hydroxy-2,2,6-6-tetramethylpiperidinoxyl is used as the N-oxyl compound, since the stabilizer system is established without containing any metal in the component thereof, the equipment eliminates the possibility of incurring corrosion of metal and facilitates the disposal of waste water.

As typical examples of the N-hydroxy-2,2,6,6-tetramethylpiperidine compound, 1,4-dihydroxy-2,2,6,6-tetramethylpiperidine and 1-hydroxy-2,2,6-6-tetramethylpiperidine may be cited. These N-hydroxy-2,2,6-6-tetramethylpiperidine compounds can be used either singly or in the form of a mixture of two or more members.

As concrete examples of the 2,2,6,6-tetramethylpiperidine compound, 2,2,6,6-tetramethylpiperidine itself may be cited. Incidentally, N-hydroxy-2,2,6-6-tetramethylpiperidine compounds and 2,2,6,6-tetramethylpiperidine compounds are possibly contained as impurities in the commercially available products of N-oxyl compounds. In this case, the use of a commercially available N-oxyl compound amounts to use of this compound in combination with N-hydroxy-2,2,6,6-tetramethylpiperidine compound or 2,2,6,6-tetramethylpiperidine compound.

As concrete examples of the phenol compound, hydroquinone and p-methoxy phenol may be cited. The p-methoxy phenol proves favorable because it excels the hydroquinone in the effect in preventing polymerization particularly when it is used in combination with N-oxyl compound and a phenothiazine compound. These phenol compounds may be used in the form of a combination of two members.

As concrete examples of the phenothiazine compound, phenothiazine, bis-(α-methylbenzyl)phenothiazine, 3,7-dioctylphenothiazine, and bis-(α-dimethylbenzyl)phenothiazine may be cited.

The copper salt compounds do not need to be particularly discriminated and they may be either inorganic salts or organic salts. Various copper salt compounds are usable. As concrete examples of the copper salt compound, copper dialkyldithiocarbamates, copper acetate, copper naphthenate, copper acrylate, copper sulfate, copper nitrate, and copper chloride may be cited. These copper salt compounds may be used in a monovalent form or a divalent form. Among the copper salt compounds enumerated above, copper dialkyldithiocarbamate proves favorable from the viewpoint of the effect.

As concrete examples of the copper dialkyldithiocarbamate, copper dimethyldithio-carbamate, copper diethyldithiocarbamate, copper dipropyldithiocarbamate, copper dibutyldithiocarbamate, copper dipentyldithiocarbamate, copper dihexyldithiocarbamate, copper diphenyldithiocarbamate, copper methylethyldithiocarbamate, copper methylpropyldithiocarbamate, copper methylbutyldithiocarbamate, copper methylpentyldithiocarbamate, copper methylhexyldithiocarbamate, copper methylphenyldithiocarbamate, copper ethylpropyldithiocarbamate, copper ethylbutyldithiocarbamate, copper ethylpentyldithiocarbamate, copper ethylhexyldithiocarbamate, copper ethylphenyldithiocarbamate, copper propylbutyldithiocarbamate, copper propylpentyldithiocarbamate, copper propylhexyldithiocarbamate, copper propylphenyldithiocarbamate, copper butylpentyldithiocarbamate, copper butylhexyldithiocarbamate, copper butylphenyldithiocarbamate, copper pentylhexyldithiocarbamate, copper pentylphenyldithiocarbamate, and copper hexylphenyldithiocarbamate may be cited. Such dialkyldithiocarbamates may be monovalent copper salts or divalent copper salts. Among the copper dialkyldithiocarbamates enumerated above, copper dimethyldithiocarbamate, copper diethyldithiocarbamate, and copper dibutyldithiocarbamate prove favorable and copper dibutyldithiocarbamate proves particularly advantageous from the viewpoint of the effect and the availability.

As concrete examples of the manganese salt compound, manganese dialkyldithiocarbamate (the alkyl group may be any of methyl, ethyl, propyl, and butyl and, in the occurrence of a plurality of alkyl groups, may be the same or different), manganese diphenyldithiocarbamate, manganese formate, manganese acetate, manganese octanoate, manganese naphthenate, and manganates of ethylenediamine tetraacetic acid may be cited. These manganese salt compounds may be used either singly or in the form of a combination of two or more members.

In this invention, the polymerization inhibitor favorable for the invention can be properly selected, depending on the kind of the surface treatment performed on the packing, the mode of use of the packed column, and the kind of the solvent to be used. Particularly, it is effective to use a polymerization inhibitor liable to volatilize on the packing filling the gas phase side in combination with a polymerization inhibitor manifesting the effect thereof on the gas phase side. As the polymerization inhibitor liable to volatilize or the polymerization inhibitor manifesting the effect thereon on the gas phase side, nitroso compounds are available. They are preferred to be thrown into the packed column.

The amount of the polymerization inhibitor to be used does not need to be particularly discriminated but may be properly adjusted to suit the conditions of the operation of the packed column. Properly, the total amount of the polymerization inhibitor to be used is fixed in the range of 3–3500 ppm (on the weight basis) relative to the mass of the (meth)acrylic acid in the reaction gas to be collected. As regards the proper amount of the individual polymerization inhibitor to be used, the amount of an N-oxyl compound is in the range of 1–500 ppm relative to the mass of the acrylic gas in the reaction gas, that of a manganese salt compound or the copper salt compound is in the range of 1–200 ppm relative to the mass of the acrylic acid in the reaction gas, that of a nitroso compound in the range of 1–500 ppm, that of a phenol compound in the range of 1–500 ppm, that of a phenothiazine compound in the range of 1–500 ppm, that of an N-hydroxy-2,2,6,6-tetramethylpiperidine compound in the range of 1–500 ppm, and that of a 2,2,6,6-tetramethylpiperidine compound in the range of 1–500 ppm.

Further, though the site for the supply of the polymerization inhibitor and the method for administration do not need to be particularly discriminated, the polymerization inhibitor is preferred to be supplied to the collecting column through the top thereof. When the polymerization inhibitor is supplied after it has been mixed with a solvent, the supply of this mode is effective in enabling the polymerization inhibitor to be uniformly dispersed in the interior of the collecting column. The solvent to be used is preferred to be a collection solvent or acrylic acid. It is economical to reclaim the collection solvent which has been separated in the purifying column.

As regards the addition of the polymerization inhibitor in the case of the purifying step, it is commendable to add the polymerization inhibitor in the amount specified above relative to the amount of the vapor of (meth)acrylic acid produced by evaporation. The expression "amount of the vapor evaporated" means the total amount of the vapor of the monomer generated by the evaporation. The total amount of the monomer vapor can be easily found by calculation and constitutes itself the numeral which serves as an important factor in the decision of the standard for the introduction of the polymerization inhibitor.

The second aspect of this invention concerns a method for the production of (meth)acrylic acid or an ester thereof, characterized by purifying in a packed column stuffed with a packing having at least part of the surface thereof subjected to a wetting treatment or a water-repelling treatment at least one member selected from the group consisting of acrylic acid, methacrylic acid, and esters thereof in the presence of a polymerization inhibitor.

This invention, by subjecting the surface of the packing to a treatment for precluding stagnation of an easily polymerizing substance-containing solution, is enabled to prevent the occurrence of a polymer on the surface of the packing and consequently permit continuous production of an easily polymerizing substance for a long time.

As the treatment to be performed on the surface of the packing for the purpose of precluding the stagnation of the easily polymerizing substance-containing solution, the water-repelling treatment, i.e. a treatment for adjusting the magnitude of Ry to a level of not more than 12.5 as specified in JIS B601, for example. The packed column described above can be used for implementing the method of production contemplated by this invention.

This invention is characterized by purifying a solution containing at least one compound selected from the group consisting of acrylic acid, methacrylic acid, and esters thereof in a packed column having disposed therein a packing having the surface thereof subjected to a treatment for precluding the stagnation of an easily polymerizing substance-containing solution. The amount of the easily polymerizing substance-containing solution to be supplied to the packed column, the pressure condition and the temperature condition for the packed column, and other conditions may be the same as those heretofore known to the art.

As the acrylic acid-containing solution, for example, an acrylic acid-containing gas obtained by the gas phase catalytic oxidation of propylene and/or acrolein is made to contact water so as to collect the acrylic acid in the form of an aqueous acrylic acid solution and this aqueous acrylic acid solution is supplied to the packed column stuffed with the packing mentioned above so as to be purified therein.

The size of the packed column, the amount of the packing to be disposed therein, and other similar conditions may be the same as those heretofore known to the art. As regards the method for stuffing the packed column with the packing, however, it is proper to continue placing the packing piecemeal on a packing support with the point of landing of the packing constantly changed while preventing the placed packing from forming heaps lest the completed packing should impart a drift current to the liquid under treatment and the packing itself should be spread unevenly. When the packing is liable to deform during the work of stuffing, it is commendable to fill the interior of the packed column in advance with water and allow the packing to fall down into the water.

In this invention, it is generally proper to add to the packed column a polymerization inhibitor for the easily polymerizing substance to be treated. Particularly when the wetting treatment has been performed as mentioned above for the purpose of preventing the surface of the packing from generating a polymer, the polymerization can be effectively prevented because the solution adhering to the surface of the packing contains the polymerization inhibitor.

The polymerization inhibitor which is usable herein, the amount there of to be used, and the method for administration may be the same as those described in the first aspect of this invention.

In the production of methacrylic acid and (meth)acrylic esters, the polymerization inhibitor can be used similarly by adopting the known conditions of production.

EXAMPLES

Now, this invention will be described more specifically below by adducing working examples.

Example 1

Acrylic acid was purified by using a packed column measuring 900 mm in inside diameter and stuffed irregularly with a packing obtained by giving a surface treatment with an alumina shot blast to cascade mini rings of stainless steel (SUS 316) made by Dodwell Industrial Corp. And sold under the product code of "No. 2P.

The packing was given a surface treatment in the form of a wetting treatment. Before the packing was disposed in a packed column, the surface thereof was wetted with water and examined to determine the degree with which the surface treatment was performed. It was consequently confirmed that the whole surface was wetted fully satisfactorily and was in a state suffering from no repellence of liquid. In contrast, the packing which had undergone no wetting treatment was found to form on the surface thereof a mixture of wetted parts and liquid-repelling parts.

A packing bed was formed in a height of 5000 mm. The packing which had undergone no surface treatment was disposed in the upper depth of 2500 mm of the bed and the packing which had undergone a surface treatment was disposed in the remainder of the bed.

The acrylic acid-containing liquid subjected to distillation comprised 65 wt. % of acrylic acid, 30 wt. % of water, and 3 wt. % of acetic acid. It was introduced into the packed column at a rate of 19,000 kg/hr from the column top and was purified under the conditions of 68° C. of column top temperature, 200 kPa of column top pressure, 78° C. of column bottom temperature, 275 kPa of column bottom pressure, and 17,800 kg/hr of the amount of extraction from the column bottom. The column was continuously operated for six months and then opened to inspect the interior thereof.

The inspection consequently revealed that in the packed bed which had undergone no surface treatment, a total of about 30 liters of a polymer was deposited on the surface of the packing and a total of only about 3 liters of a polymer was deposited on the packing which had undergone a heat treatment.

Example 2

In addition to the procedure of Example 1, 400 ppm (based on the concentration of acrylic acid in the feed material) of hydroquinone was introduced as a polymerization inhibitor into the column via the top thereof.

The column was continuously operated for six months and then opened to inspect the interior thereof. The inspection consequently revealed that in the packed bed which had undergone no heat treatment, a total of about 15 liters of a polymer was deposited on the surface of the packing and absolutely no polymer was detected on the packing which had undergone a surface treatment.

Example 3

The distillation of Example 1 was performed by faithfully following the procedure of Example 1 while stuffing a packed column with a packing which had undergone a water-repelling treatment for adjusting the surface roughness, Ry, of the packing to a level of not higher than 12.5 as specified in JIS B601.

The inspection given similarly to the interior of the packed column consequently revealed that in the packed bed which had undergone no surface treatment, a total of about 80 liters of a polymer was deposited on the surface of the packing and a total of only about 5 liters of a polymer was deposited on the packing which had undergone a surface treatment.

Example 4

Acrylic acid was purified by using a packed column measuring 900 mm in inside diameter and stuffed irregularly with a packing obtained by giving a surface treatment with an alumina shot blast to cascade mini rings of stainless steel (SUS 316) made by Dodwell Industrial Corp. And sold under the product code of "No. 2P.

The packing was given a surface treatment in the form of a wetting treatment. Before the packing was disposed in a packed column, the surface thereof was wetted with water and examined to determine the degree with which the surface treatment was performed. It was consequently confirmed that the whole surface was wetted fully satisfactorily and was in a state suffering from no repellence of liquid. In contrast, the packing which had undergone no wetting treatment was found to form on the surface thereof a mixture of wetted parts and liquid-repelling parts.

A packing bed was formed in a height of 5000 mm. The packing which had undergone no surface treatment was disposed in the lower depth of 2500 mm of the bed and the packing which had undergone a surface treatment was disposed in the remainder of the bed.

The acrylic acid-containing liquid subjected to distillation comprised 65 wt. % of acrylic acid, 30 wt. % of water, and 3 wt. % of acetic acid. It was introduced into the packed column at a rate of 19,000 kg/hr from the column top and was purified under the conditions of 68° C. of column top temperature, 200 kPa of column top pressure, 78° C. of column bottom temperature, 275 kPa of column bottom pressure, and 17,800 kg/hr of the amount of extraction from the column bottom. The column was continuously operated for six months and then opened to inspect the interior thereof.

The inspection consequently revealed that in the packed bed which had undergone no surface treatment, a total of about 40 liters of a polymer was deposited on the surface of the packing and a total of only about 2 liters of a polymer was deposited on the packing which had undergone a heat treatment.

Example 5

The distillation of Example 4 was performed by faithfully following the procedure of Example 4 while stuffing a packed column with a packing which had undergone a water-repelling treatment for adjusting the surface roughness, Ry, of the packing to a level of not higher than 12.5 as specified in JIS B601.

The inspection given similarly to the interior of the packed column consequently revealed that in the packed bed which had undergone no surface treatment, a total of about 100 liters of a polymer was deposited on the surface of the packing and a total of only about 5 liters of a polymer was. deposited on the packing which had undergone a surface treatment.

What is claimed is:

1. A method for preventing an easily polymerizing substance from exposing the substance to polymerization in a packed column handling the easily polymerizing substance, by subjecting the surface of a packing disposed in the interior of the column to a water repelling treatment or a wetting treatment.

2. A method according to claim 1, wherein said water-repelling treatment consists in adjusting the surface roughness, Ry, of part or the whole of the surface of said packing to a level of not more than 12.5 as specified in JIS B601.

3. A method according to claim 1, wherein said wetting treatment consists in shot blast.

4. A method according to claim 1, wherein the shape of said packing is at least one kind selected from the group consisting of rasching rings, Lessing rings, pall rings, flexirings, cascade mini rings, rasching super rings, intalox metal tower packings, and interlock saddles.

5. A method according to claim 1, wherein the surface of the content of the column other than the packing disposed in the packed column has the magnitude of Ry adjusted to a level of not higher than 12.5 as specified in JIS B601.

6. A method according to claim 1, which further comprises adding a polymerization inhibitor to the interior of said packed column.

7. A method for the production of (meth)acrylic acid or an ester thereof, characterized by purifying at least one member selected from the group consisting of acrylic acid, methacrylic acid, and esters thereof in the presence of a polymerization inhibitor in a packed column having disposed therein a packing having at least part of the surface thereof subjected to a wetting treatment or a water-repelling treatment.

* * * * *